United States Patent [19]

Ishiguro et al.

[11] Patent Number: 5,026,844
[45] Date of Patent: Jun. 25, 1991

[54] PROCESS FOR THE PREPARATION OF 4-ACYLOXY-2-AZETIDINONE DERIVATIVES

[75] Inventors: Masaji Ishiguro, Osaka; Hiromitsu Iwata, Takatsuki; Takashi Nakatsuka, Mishima; Yasuo Yamada, Takaoka, all of Japan

[73] Assignees: Suntory Limited, Osaka; Nippon Soda Company, Ltd., Tokyo, both of Japan

[21] Appl. No.: 421,331

[22] Filed: Oct. 13, 1989

[30] Foreign Application Priority Data

Oct. 19, 1988 [JP] Japan ............................... 63-263766
Oct. 11, 1989 [JP] Japan ................................. 1-264193

[51] Int. Cl.$^5$ .................. C07D 205/085; C07B 41/12
[52] U.S. Cl. ..................................................... 540/357
[58] Field of Search ......................................... 540/357

[56] References Cited

PUBLICATIONS

Chemical and Pharmaceutical Bulletin, vol. 29, No. 10, Oct. 1981, pp. 2899–2909, A. Yoshida et al.: "2-(Alkylthio)Penem-3-Carboxylic Acids. IV. Synthesis of (Hydroxyethyl)-Azetidinone Precursors to 1-Thia Analogs. . .".
Tetrahedron Letters, vol. 27, No. 29, 1986, pp. 2315–2318, C. J. Easton et al., "Direct Introduction of a Benzoyloxy Substitutent at the C-4 Position . . .".
The Journal of Chemical Society, Chemical Communications, 1979, pp. 485, 486, H. Matsumura et al., "Direct Introduction of a Benzoyloxy Substitutent . . . ".
Synthetic Methods of Organic Chemistry, vol. 25, 1971 p. 164, Abstract 199, W. Theilheimer; "Alpha-Ketoaldehydes from 1-Hydroxy-2-Ketothioethers".
The Journal of Organic Chemistry, vol. 48, No. 22, Nov. 4, 1983, pp. 4043–4048, M. L. M. Pennings et al.,: "Chemistry of Four-Membered Cyclic Nitrones. 5. Synthesis and Oxidation of 1-Hydroxyazetidines".
Synthetic Methods of Organic Chemistry, vol. 29, 1975, p. 121, Abstract No. 215, "Glycosides from Thioglycosides with Anomerization".
C. J. Easton, J. Chem. Soc., Perkins I, 277 (1990).
van Elburg, Hetereocycles 26, 437 (1987).
Yoshida Chem. Pharm. Bull. 29 (10) 2899–2909 (1981).
Fuchigami, Chem. Abs. 107, 153936n (1987).
Ferrholz, Chem. Abs. 86, 29377q.

Primary Examiner—Mark L. Berch
Attorney, Agent, or Firm—Oblon, Spivak, McClelland, Maier & Neustadt

[57] ABSTRACT

A process for producing 3-[1'-(R)-hydroxyethyl]-4-acyloxyazetidinone from 3-[1'-(R)-hydroxyethyl]-4-alkyl (or aryl) thioazetidinone using a copper salt of aliphatic or aromatic carboxylic acid is disclosed. The process is an effective route for producing 3-[1'-(R)-hydroxyethyl]-4-acyloxyazetidinone, and intermediate for synthesizing penems or carbapenems, without using a mercury salt which can cause an environmental hazard.

9 Claims, No Drawings

PROCESS FOR THE PREPARATION OF 4-ACYLOXY-2-AZETIDINONE DERIVATIVES

BACKGROUND OF THE INVENTION

1. Field of the Invention

The present invention relates to a novel process for preparing 4-acyloxy-2-azetidinone derivatives which are useful as intermediates for synthesizing penems or carbapenems.

2. Description of the Background Art

3-[1'-(R)-hydroxyethyl]-4-acyloxyazetidinone as well as its derivatives with the hydroxy group or the β-lactam NH group being protected by any one of various protecting groups are used as excellent intermediates for synthesizing penems or carbapenems. Several reports have appeared on the processes for preparing these compounds [e.g. N. Ueyama et al. Japanese Patent Laid-open No. 84057/1987; M. Shiozaki et al. Tetrahedron Lett., 22, 5205 (1981)].

Processes for preparing 3-[1'-(R)-hydroxyethyl]-4-arylthioazetidinone derivatives are also reported (e.g. M. Ishiguro et al. Japanese Patent Laid-open No. 207373/1986; S. Gerard et al. Japanese Patent Laid-open No. 97280/1986 and M. Shibazaki et al. Japanese Patent Laid-open No. 44355/1984). These arylthio derivatives are usually converted into 4-acyloxy or 4-arylsulfone compounds, which are used for the preparation of 3-[1'-(R)-hydroxyethyl]-4-acyloxyazetidinone or its derivatives. Conversion into compounds with an acyloxy group is more desirable because of their higher reactivity. A process using a mercury salt is reported for converting the arylthio derivatives into compounds having an acyloxy group (A. Yoshida et al. Chem. Pharm. Bull, 29, 2899).

The process using a mercury salt is, however, not suitable for industrial application because of the toxicity of mercury salts. There has therefore been a strong need for the development of a process using another less toxic compound.

The present inventors have undertaken extensive studies in order to develop a process for converting 3-[1'-(R)-hydroxyethyl]-4-arylthioazetidinone into the more useful 3-[1'-(R)-hydroxyethyl]-4-acyloxyazetidinone without using a mercury salt. The studies have led to the completion of the present invention.

SUMMARY OF THE INVENTION

An object of the present invention is to provide a process for preparing a 4-acyloxy-2-azetidinone derivative of the following formula (II):

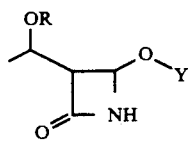

wherein OR is a protected hydroxy group and Y is an acyl group, which comprises reacting a 2-azetidinone derivative of the following formula (I):

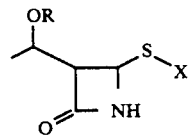

wherein OR has the same meaning as defined above and X is an alkyl group or an aromatic group, and a copper compound in the presence of an organic carboxylic acid or a salt of organic carboxylic acid as an acyl group source.

DETAILED DESCRIPTION OF THE INVENTION AND PREFERRED EMBODIMENTS

Since the alkyl or aromatic group represented by X of the formula (I) is released by the reaction from the compound together with the adjacent S, it can be any alkyl or aromatic group so long as it does not interfere with the reaction. In view of the availability and the commercial aspect, preferable groups are lower alkyl groups having $C_{1-4}$ carbon atoms such as methyl, ethyl, propyl, and butyl groups; aromatic groups such as phenyl, alkylphenyl, or alkoxyphenyl groups having an alkyl or alkoxy, group of $C_{1-4}$ carbon atoms; halophenyl groups; and the like.

Examples of the protected hydroxy group represented by OR include tert-butyldimethylsililoxy, tert-butyldiphenylsililoxy, dimethylcumylsililoxy, triisopropylsililoxy, dimethylthexylsililoxy, p-nitrobenzyloxycarbonyloxy, p-methoxybenzyloxycarbonyloxy, and allyloxycarbonyloxy groups.

The acyl group represented by Y is that derived from an organic carboxylic acid or a salt of organic carboxylic acid which is to be included in the reaction mixture, and can be exemplified by acetyl, chloroacetyl, trichloroacetyl, fluoroacetyl, trifluoroacetyl, propionyl, benzoyl, halobenzoyl, and methoxybenzoyl groups.

Copper oxides and copper salts of organic carboxylic acids can be used as copper compounds. Examples of preferable copper salts of organic carboxylic acid are copper salts of aliphatic carboxylic acids such as copper (I) acetate, copper (II) acetate, copper propionate, copper butyrate, and the like, and copper salts of aromatic carboxylic acid such as copper benzoate, and the like.

An organic carboxylic acid or its salts are used as an acyl group source. Examples are aliphatic carboxylic acids such as acetic acid, chloroacetic acid, trichloroacetic acid, fluoroacetic acid, trifluoroacetic acid, propionic acid, butyric acid, and the like; aromatic carboxylic acids such as benzoic acid, and the like, and salts of carboxylic acid such as sodium, potassium; and ammonium carboxylates.

A copper salt of the organic carboxylic acids mentioned above as examples of a copper compound can be, at the same time, an acyl group source in this invention.

In the process of the present invention, a compound of formula (I) is reacted with a copper compound in the presence of an aromatic or aliphatic carboxylic acid in a free or salt form as an acyl group source.

When the reaction of a compound of formula (I) and a copper compound is carried out using an aliphatic carboxylic acid such as acetic acid or an aromatic carboxylic acid such as benzoic acid as a solvent, such a carboxylic acid can function as an acyl group source.

The above-mentioned copper compounds can also be an acyl group source.

If desired, a compound of formula (I) can be reacted with a copper salt of organic carboxylic acid in an organic carboxylic acid solvent.

Also, if desired, a salt of an organic carboxylic acid other than a copper salt may be present in the reaction mixture.

Solvents other than organic carboxylic acids which can be used are, for example, dimethylformamide, acetonitrile, dimethylacetamide, dimethylsulfoxide, methylene chloride, and the like.

The amount of the copper compound to be used in the reaction is preferably a 0.5 equivalent or greater, and more preferably a 0.5–0.65 equivalent, to 1 mole of the compound of formula (I).

The reaction can be carried out under the atmospheric condition, but preferably under argon or nitrogen atmosphere. A preferable reaction temperature varies depending on the types of copper compound and organic carboxylic acid used. Usually, the reaction temperature is selected from the range between 0° C. and the boiling point of the solvent used.

After completion of the reaction, deposited insoluble products are collected by filtration. The filtrate is diluted with an organic solvent such as ethyl ether, ethyl acetate, chloroform, or the like, and washed with an alkaline aqueous solution such as an aqueous solution of sodium bicarbonate to neutralize it. The organic layer is concentrated to produce a compound of formula (I) as crystals. The product can be purified by column chromatography, fractionation thin layer chromatography, recrystallization, or the like means.

Other features of the invention will become apparent in the course of the following description of the exemplary embodiments which are given for illustration of the invention and are not intended to be limiting thereof.

EXAMPLES

EXAMPLE 1

Synthesis of (1'R, 3R, 4R)-3-(1'-tert-butyldimethyl-sililoxy)ethyl-4-acetoxy-2-azetidinone

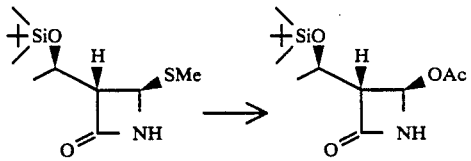

A mixture of 74 mg (0.25 mmol) of (1'R, 3S, 4R)-3-(1'-tert-butyldimethylsililoxy)ethyl-4-methylthic-2-azetidinone and 30 mg (0.15 mmol) of copper (II) acetate monohydrate in 0.5 ml of acetic acid was heated at 120° C. for 30 minutes with stirring. The reaction mixture was diluted with ether and the insoluble materials were filtered off. The organic layer was washed with saturated sodium bicarbonate solution and then water, dried, and concentrated to produce 46 mg (yield: 64.0%) of the title compound as white crystals. NMR (CDCl₃, TMS, 270 MHz : 0.061 (s, 3H), 0.076 (s, 3H), 0.867 (s, 9H), 1.25 (3H, d, 6.6 Hz), 2.108 (s, 3H), 3.18 (d, 1H, 3.4 Hz), 4.18–4.26 (m, 1H), 5.84 (m, 1S), 6.7 (br, S, 1H)

EXAMPLE 2

Synthesis of (1'R, 3R, 4R)-3-(1'-tert-butyldimethyl-sililoxy)ethyl-4-acetoxy-2-azetidinone

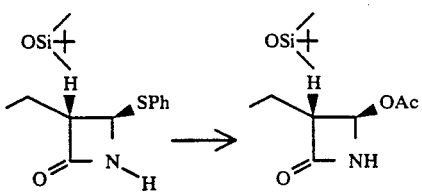

A mixture of 337 mg (1 mmol) of (1'R, 3, 4R)-3-(1'-tert-butyldimethylsililoxy)ethyl-4-phenylthic-2-azetidinone and 102 mg (0.5 mmol) of copper (II) acetate monohydrate in 2 ml of acetic acid was heated at 100° C. for 45 minutes with stirring. The reaction mixture was diluted with ether and the insoluble materials were filtered off. The filtrate was washed with saturated sodium bicarbonate solution and then water, dried, and concentrated. The residue was purified by silica gel column chromatography to produce 247 mg (yield: 85.9%) of the title compound.

EXAMPLE 3

Synthesis of (1'R, 3R, 4R)-3-(1'-tert-butyldimethyl-sililoxy)ethyl-4-benzoyloxy-2-azetidinone

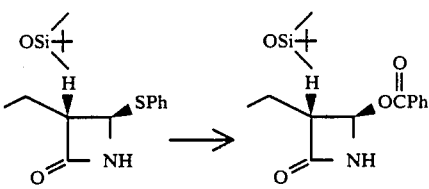

To a mixture of 337 mg (1 mmol) of (1'R, 3S, 4R)-3-(1'-tert-butyldimethylsililoxy)ethyl-4-phenylthio-2-azetidinone, 1 mmol of copper (II) benzoate, and 2 ml of dimethylformamide was added 244 mg (2 mmol) of benzoic acid. The mixture was heated at 70° C. for 30 minutes with stirring. Ether was added to the reaction mixture and the insoluble materials were filtered off. The filtrate was washed with saturated sodium bicarbonate solution and then water, dried, and purified by silica gel column chromatography (eluent: hexane/ethyl acetate=3/1) to produce 60 mg (yield: 17.2%) of the title compound.

NMR (CDCl₃, TMS, 270 MHz): 0.09 (s, 3H), 0.10 (s, 3H), 0.88 (s, 9H), 1.31 (d, 3H, J=6.6 Hz), 3.36 (d, 3H, J=3.3 Hz), 4.27–4.30 (m, 1H), 6.11 (S, 1H), 6.65 (br, S, 1H, 7.46 (t, 2H, J=8.0 Hz), 7.61 (t, 1H, J=7.2 Hz), 8.05 (d, 2H, J=7.2 Hz

EXAMPLE 4

Synthesis of (1'R, 3R, 4R)-3-(1'-tert-butyldimethylsililoxy)ethyl-4-acetoxy-2-azetidinone

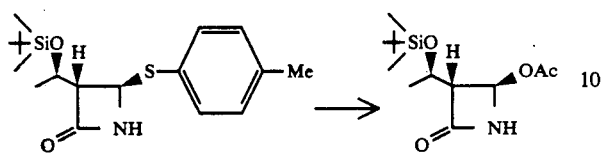

A mixture of 351 mg (1 mmol) of (1'R, 3S, 4R)-3-(1'-tert-butyldimethylsililoxy)ethyl-4-p-methylphenylthio-2-azetidinone and 100 mg (0.5 mmol) of copper (II) acetate monohydrate in 2 ml of acetic acid was heated at 110° C. for 5 minutes with stirring. The reaction mixture was diluted with ether and the insoluble materials were filtered off. The filtrate was washed with saturated sodium bicarbonate solution and then water, dried, and concentrated to produce 223 mg (yield: 77.6%) of the title compound as white crystals.

EXAMPLE 5

Synthesis of (1'R, 3R, 4R)-3-(1'-tert-butyldimethyl-sililoxy)ethyl-4-acetoxy-2-azetidinone

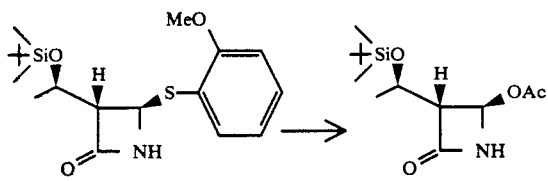

A mixture of 367 mg (1 mmol) of (1'R, 3S, 4R)-3-(1'-tert-butyldimethylsililoxy)ethyl-4-o-methoxphenylthio-2-azetidinone and 100 mg (0.5 mmol) of copper [II] acetate monohydrate in 2 ml of acetic acid was heated at 110° C. for 5 minutes with stirring. The reaction mixture was diluted with ether and the insoluble materials were filtered off. The filtrate was washed with saturated sodium bicarbonate solution and then water, dried, and concentrated to produce 214 mg (yield: 77.5%) of the title compound as white crystals.

EXAMPLE 6

Synthesis of (1'R, 3R, 4R)-3-(1'-tert-butyldimethyl-sililoxy)ethyl-4-acetoxy-2-azetidinone

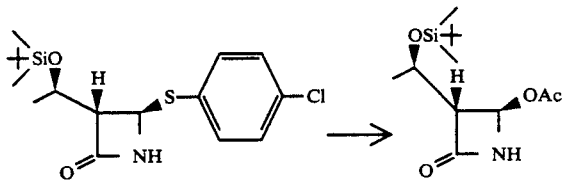

A mixture of 372 mg (1 mmol) of (1'R, 3S, 4R-3-(1'-tert-butyldimethylsililoxy)ethyl-4-p-chlorophenylthio-2-azetidinone and 100 mg (0.5 mmol) of copper (II) acetate monohydrate in 2 ml of acetic acid was heated at 110° C. for 25 minutes with stirring. After cooling, the reaction mixture was diluted with ether and the insoluble materials were filtered off. The filtrate was washed with saturated sodium bicarbonate solution and then water, dried, and concentrated to produce 200 mg (yield: 69.6%) of the title compound as white crystals.

EXAMPLE 7

Synthesis of (1'R, 3R, 4R)-3-(1'-tert-butyldimethyl-sililoxy)ethyl-4-acetoxy-2-azetidinone

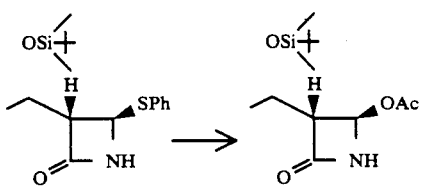

A reaction vessel was replaced with argon and to this were added 10.11 g (30 mmol) of (1'R, 3S, 4R]-3-(1'-tert-butyldimethylsililoxy)ethyl-4-phenylthio-2-azetidinone and 2.86 g (20 mmol) of copper (I) acetate and 90 ml of acetic acid. The mixture was heated at 25° C. for 3 hours with stirring. 5 g of Hyflo Super-Cel (Johns-Manville Sales Corp.) was added and the mixture was filtered. The residue was washed with 30 ml of acetic acid. The filtrate and the washing were concentrated together under reduced pressure to obtain 13 g of a residue. 90 ml of methylene chloride was added to the residue and the mixture was washed with 45 ml of saturated sodium bicarbonate solution. The organic layer was washed with 45 ml of water, and concentrated to a 47 g weight. After the addition of 60 ml of isooctane the mixture was further concentrated to obtain 36 g of a residue, which was cooled to 0° C. The deposit thus produced was gathered by filtration and dried to obtain 7.84 g of the title compound as white crystals. The purity of the product by HPLC. analysis was 100% (yield: 91%).

EXAMPLE 8

Synthesis of (1'R, 3R, 4R)-3-(1'-tert-butyldimethyl-sililoxy)ethyl-4-acetoxy-2-azetidinone

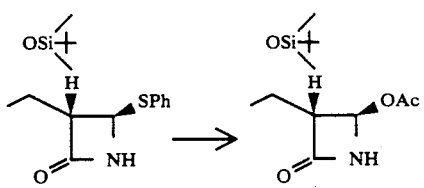

A reaction vessel was replaced with argon and to this were added 10.11 g (30 mmol) of (1'R, 3S, 4R)-3-(1'-tert-butyldimethylsililoxy)ethyl-4-phenylthio-2-azetidinone and 2.86 g (20 mmol) of copper (I) acetate and 60 ml of methylene chloride. To the mixture were added 2.40 g (40 mmol) of acetic acid and 5 ml of acetonitriles and the mixture was refluxed (at 41° C.) for 6 hours with stirring. After cooling, 5 g of Hyflo Super-Cel was added and the mixture was filtered. The residue was washed with 30 ml of acetic acid. The filtrate and the washing were washed together with 45 ml of saturated sodium bicarbonate solution. The same procedure as in Example 7 was performed on the organic layer to produce 7.92 g of the title compound. The purity of the product by HPLC analysis was 100% (yield: 92%).

REFERENCE EXAMPLE

Synthesis of (1'R, 3R, 4R)-3-(1'-tert-butyldimethyl-sililoxy)ethyl-4-acetoxy-2-azetidinone

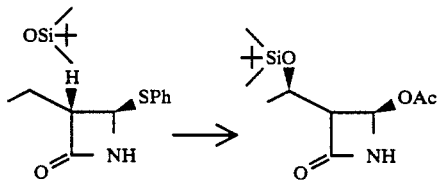

A mixture of 337 mg (1 mmol) of (1'R, 3S, 4R)-3-(1'-tertbutyldimethylsililoxy)ethyl-4-phenylthic'-2-azetidinone and 223 mg (0.7 mmol) of mercury (II) acetate in 2 ml of acetic acid was stirred at room temperature for 10 minutes. The reaction mixture was diluted with ether and the insoluble materials were filtered off. The filtrate was washed with saturated sodium bicarbonate solution, 5% aqueous solution of sodium sulfate, and then water, dried over anhydrous sodium sulfate, and concentrated. The residue was purified by silica gel column chromatography to produce 287 mg (yield: 99.8%) of the title compound.

3-[1'-(R)-hydroxyethyl)-4-alkyl (or aryl) thioazetidinone can be converted into 3-[1'-(R)-hydroxyethyl)-4-acyloxyazetidinone by the process of the present invention with a high efficiency without using a mercury salt which can cause an environmental hazard.

Obviously, numerous modifications and variations of the present invention are possible in light of the above teachings. It is therefore to be understood that within the scope of the appended claims. The invention may be practiced otherwise than as specifically described herein.

What is claimed is:

1. A process for preparing a 4-acyloxy-2-azetidinone derivative having the formula (II):

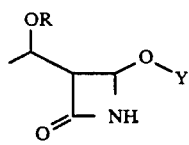 (II)

wherein OR is a protected hydroxy group and Y is an acyl group, which comprises reacting a 2-azetidinone derivative having the formula (I):

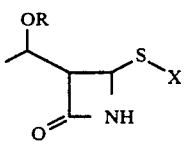 (I)

wherein OR has the same meaning as defined above and X is an alkyl group or an aromatic group, and a copper oxide or copper salt of an organic carboxylic acid, in the presence of an organic carboxylic acid or a salt thereof as an acyl group source.

2. A process for preparing a 4-acyloxy-2-azetidinone derivative according to claim 1, wherein said 2-azetidinone derivative is an optical isomer at the 1'-, 3-, or 4-position, or any combination thereof, and the 4-acyloxy-2-azetidinone derivative prepared therefrom is the corresponding optical isomer.

3. A process for preparing a 4-acyloxy-2-azetidinone derivative according to claim 1, wherein said organic carboxylic acid is an aliphatic carboxylic acid or an aromatic carboxylic acid.

4. A process for preparing a 4-acyloxy-2-azetidinone derivative according to claim 2, wherein said organic carboxylic acid is an aliphatic carboxylic acid or an aromatic carboxylic acid.

5. A process for preparing a 4-acyloxy-2-azetidinone derivative according to claim 1, wherein a copper salt of organic carboxylic acid is used as a copper compound, and, at the same time, as an acyl group source.

6. A process for preparing a 4-acyloxy-2-azetidinone derivative according to claim 5, wherein said copper salt of organic carboxylic acid is a copper salt of aliphatic carboxylic acid or a copper salt of aromatic carboxylic acid.

7. A process for preparing a 4-acyloxy-2-azetidinone derivative according to claim 5, wherein said copper salt of organic carboxylic acid is copper (I) acetate, copper (II) acetate, copper propionate, copper butyrate, or copper benzoate.

8. A process for preparing a 4-acyloxy-2-azetidinone derivative as claimed in claim 1 wherein said copper salt of an organic carboxylic acid is chosen from the group consisting of copper (I) acetate, copper (II) acetate, copper propionate, copper butyrate, and copper benzoate.

9. A process for preparing a 4-acyloxy-2-azetidinone derivative as claimed in claim 1 wherein said organic carboxylic acid or salt thereof is chosen from the group consisting of acetic acid, chloroacetic acid, trichloroacetic acid, fluoroacetic acid, trifluoroacetic acid, propionic acid, butyric acid, halobenzoic acid, and methoxybenzoic acid.

* * * * *